(12) United States Patent
Shao et al.

(10) Patent No.: US 9,833,485 B2
(45) Date of Patent: Dec. 5, 2017

(54) LACTOBACILLUS PLANTARUM CAPSULE FOR POULTRY AND USE THEREOF

(71) Applicant: BEIJING KEHUITONGZHIHUI TECHNOLOGY CO., LTD., Beijing (CN)

(72) Inventors: Suying Shao, Beijing (CN); Jianshu Li, Beijing (CN)

(73) Assignee: Ningxia RisingMark Intellectual Property Consulting Co., Ltd, Ningxia (CN)

( * ) Notice: Subject to any disclaimer, the term of this patent is extended or adjusted under 35 U.S.C. 154(b) by 11 days.

(21) Appl. No.: 14/886,397

(22) Filed: Oct. 19, 2015

(65) Prior Publication Data

US 2016/0038547 A1 Feb. 11, 2016

(30) Foreign Application Priority Data

Oct. 21, 2014 (CN) .......................... 2014 1 0563261

(51) Int. Cl.

| | |
|---|---|
| *A61K 35/747* | (2015.01) |
| *A61K 36/062* | (2006.01) |
| *A61K 9/48* | (2006.01) |
| *A61K 38/16* | (2006.01) |
| *A23K 40/30* | (2016.01) |
| *A23K 10/18* | (2016.01) |
| *A23K 20/147* | (2016.01) |
| *A23K 20/163* | (2016.01) |
| *A23K 50/75* | (2016.01) |
| *A23K 50/30* | (2016.01) |
| *A23K 50/60* | (2016.01) |

(52) U.S. Cl.
CPC ............ *A61K 35/747* (2013.01); *A23K 10/18* (2016.05); *A23K 20/147* (2016.05); *A23K 20/163* (2016.05); *A23K 40/30* (2016.05); *A23K 50/30* (2016.05); *A23K 50/60* (2016.05); *A23K 50/75* (2016.05); *A61K 9/4816* (2013.01); *A61K 9/4825* (2013.01); *A61K 9/4833* (2013.01); *A61K 9/4858* (2013.01); *A61K 9/4866* (2013.01); *A61K 9/4875* (2013.01); *A61K 36/062* (2013.01); *A61K 38/168* (2013.01); *A23Y 2220/67* (2013.01)

(58) Field of Classification Search
CPC .. A61K 35/747; A61K 36/062; A61K 9/4833; A61K 9/4875; A61K 9/4858; A61K 9/4866; A61K 9/4816; A61K 9/4825; A61K 38/168; A23K 40/30; A23K 10/18; A23K 20/163; A23K 50/75; A23K 50/30; A23K 50/60; A23Y 2220/67

See application file for complete search history.

(56) References Cited

FOREIGN PATENT DOCUMENTS

| CN | 1569043 A | 1/2005 |
|---|---|---|
| CN | 1613455 A | 5/2005 |
| CN | 101496555 A | 8/2009 |
| CN | 103798810 A | 5/2014 |

OTHER PUBLICATIONS

Petrovic et al. "Protection of Probiotic Microorganisms by Microencapsulation" (2007) Chem Industry & Chem Engineer Quarterly, vol. 13, No. 3: 169-174.*

Capela et al. "Effect of cryoprotectants, prebiotics and microencapsulation of bacterial cells in improving the viability of probiotic organisms in freeze-dried yoghurt." (2006) Victoria University, MS in Food Science thesis, 1-42.*

* cited by examiner

*Primary Examiner* — Robert Yamasaki
*Assistant Examiner* — Teresa E Knight
(74) *Attorney, Agent, or Firm* — Michael Ye; Andrews Kurth Kenyon LLP

(57) ABSTRACT

The present invention relates to a *Lactobacillus plantarum* capsule and use thereof, and belongs to the technical field of microbe feed additives. The *Lactobacillus plantarum* capsule consists of a wall material, *Lactobacillus plantarum*, a cryoprotectant, stachyose, and *Morchella esculenta* zymolytic powders; wherein the wall material is composed of zymolytic soybean protein isolate, chitosan, xanthan gum, carrageenin, glycerin and trehalose, and when formulated into a mixed solution, the above substances have concentrations of 7 to 10% zymolytic soybean protein isolate, 1 to 2% chitosan, 1 to 3% xanthan gum, 0.1 to 0.5% carrageenin, 0.3 to 1% glycerin, and 0.5 to 2% trehalose. The *Lactobacillus plantarum* capsule of the present invention enhances resistance of the capsule to gastric acid, has very good enteric solubility, besides, it can effectively inhibit the growth of pathogenic germs to improve immunity, decrease incidence of diseases in livestock and poultry, and improve the breeding quality and benefit.

9 Claims, No Drawings

LACTOBACILLUS PLANTARUM CAPSULE FOR POULTRY AND USE THEREOF

This application claims priority of Chinese Application No. 2014105632614 filed on Oct. 21, 2014 and entitled "*Lactobacillus Plantarum* Capsule for Poultry and Use Thereof.

TECHNICAL FIELD

The present invention relates to a *lactobacillus* microcapsule product and use thereof, and belongs to the technical field of microbe feed additives.

BACKGROUND

The wide use of antibacterial agents such as antibiotics in animal industry has greatly promoted the development of breeding and animal industries. At present, more than 95% of premix products have antibacterial agents added therein. However, this addition also suffers from increasingly significant disadvantages in that, products of the animal industry have severe drug residues that directly harm the health of human bodies; the abuse of antibiotics causes pathogenic germs to develop drug resistance, leading to diffusion and spread of drug-resistant strains; at the same time, dysbacteriosis is caused in animal bodies, decreasing the animal immunity, deteriorating the breeding environment, and increasing diseases; and a series of severe problems such as endogenous infection as well as superinfection and cross-infection are initiated in animals. Since 2006, The European Union has began to completely prohibit the addition of antibiotics into feed, and reduce or prohibit the addition of antibacterial agents into feed. The United States also beganto prohibit the use of antibiotics in feed. Currently, universal attentions from various countries around the world have been paid to the standardization and reduction of use of antibacterial agents in breeding processes, and the development of safe and green feed additives as surrogates thereof.

The *lactobacillus* microecological feed additive is an important surrogate for antibacterial agents. *Lactobacillus* is one of outstanding representatives of beneficial bacteria in the enteric normal flora, and has important physiologic and health-care functions in that, it can antagonize pathogenic microorganism, and adjust the microflora balance of digestive tracts in animals; It can activate the immune system, enhance immunity, and prevent the occurrence of various diseases and adverse reactions; it can inhibit the occurrence of tumors, and protect the animal health; it can synthesize nutritional substances, produce digestive enzymes, increase activity of the digestive enzymes in animals, ameliorate the metabolism of vitamins, neutralize enterotoxins, and reduce the production of harmful substances such as amine and ammonia; and the like. However, *lactobacillus* forms no spores in the growth process, has poor stress resistance, and is very sensitive to external environment, for example, oxygen, moisture, elevated temperature, mechanical squeeze, heat shock and gastric acid, so that the number of viable bacteria is hard to be ensured effectively in practical use. Therefore, how to screen out excellent *lactobacillus* strains and prolong activity of commercial products thereof has always been a research and development emphasis of *lactobacillus* manufacturers over the world.

The capsule technique is one of the most effective and practical method for protecting the bacterial vitality. By encapsulation of *lactobacillus*, bacterial bodies can be separated from adverse external environment, in order to protect against impairment from microelements in the feed, and alleviate the influences from temperature and pressure in the granulating process. By the formation of solid particles, uniform distribution in the premix is favored, and storage and transportation are favored as well. By the employment of an enteric wall material, it can be further ensured that as many bacterial bodies as possible reach the intestinal tract, to allow the bacteria to actually exert health-care and therapeutic efficacy.

For example, Patent CN1613455 disclosed a probiotic microcapsule coated with a three-layer protection layer; and Patent CN1569043 disclosed a *lactobacillus* microcapsule produced by spray coating in a fluidized bed by employing sodium alginate and calcium chloride as the wall materials. The above patents increase the survival rates of probiotics or lactobacilli to certain extents. However, inevitably, in CN1613455, the temperature of hydrogenated oil and fat exceeding 55° C. may cause damage to lactobacilli inside the core material, and at the same time, the outer controlled release coating material allows the lactobacilli to fail to quickly release in the intestinal tract, thus a part of the lactobacilli will be discharged out of the body, and availability of the lactobacilli is reduced. In CN1569043, sodium alginate is employed as the wall material, which is frequently used in the coating of a microcapsule at present. However, sodium alginate itself has poor moisture holding capacity, and microcapsule gel coated with sodium alginate is liable to water loss, hardening, and cracking. In addition, microcapsules coated with sodium alginate are intolerant to gastric acid, and have poor capacity of passing through stomach. A patent named A Method for Preparing A *Lactobacillus* Powder Containing Multi-Layer Microcapsule Lactobacilli, with a patent application number of 201310743621.4, is characterized in that, 20 to 30 parts of marine fishskin collagen oligopeptide powder, 5 to 20 parts of citric acid, and 40 to 50 parts of multi-layer microcapsule *lactobacillus* powder are mixed and stirred. An invention named *Lactobacillus* Microcapsule And Preparation Method and Use Thereof, with an application number of 200810135259.1, also discloses a *lactobacillus* microcapsule and preparation methods and use thereof. The *lactobacillus* microcapsule consists of an outer wall material, a cryoprotectant and lactobacilli.

In summary, the existing microcapsule coating technique either causes a greater damaging effect on lactobacilli during its implementation process, or produces a microcapsule that has poor tolerance to the stomach environment, which are all unfavorable to the industrialization and application of microcapsule products.

SUMMARY

An objective of the present invention is to provide a *Lactobacillus plantarum* capsule product including *Lactobacillus plantarum*.

The *Lactobacillus plantarum* capsule product consists of a wall material, *Lactobacillus plantarum*, a cryoprotectant, stachyose, and *Morchella esculenta* zymolytic powders.

The wall material is composed of zymolytic soybean protein isolate, chitosan, xanthan gum, carrageenin, glycerin and trehalose; and when formulated into a mixed solution, the above substances have concentrations of 7 to 10% zymolytic soybean protein isolate, 1 to 2% chitosan, 1 to 3% xanthan gum, 0.1 to 0.5% carrageenin, 0.3 to 1% glycerin, and 0.5 to 2% trehalose, respectively.

The zymolytic soybean protein isolate is prepared by a method including: formulating a solution of soybean protein isolate at a concentration of 10 to 13%, heating to 30-45° C., adjusting the solution to pH 3-5, added therein an acid proteinase at 0.1 to 1% by weight of the soybean protein isolate for enzymolysis with heat preservation for 0.5 to 1.5 h, and then spray drying the solution to obtain the zymolytic soybean protein isolate.

The *Morchella esculenta* zymolytic powders are prepared by a method as follows:

(1) drying and pulverizing fruit bodies of *Morchella esculenta*;

(2) homogeneous dissolution in water, wherein the pulverized fruit bodies of *Morchella esculenta* are added into a stainless steel cylinder, water 3 to 6 times by weight of the fruit bodies is added therein, to soak the fruit bodies for 3 to 5 h, and then this solution of the *Morchella esculenta* fruit bodies is passed through a colloid mill, under an operation condition of: a gap between a stator and a rotor of the colloid mill adjusted to 0.5-1 μm, and a flow rate of the colloid mill at 0.4-1 t/h;

(3) enzymolysis at rised temperature, wherein the mixed solution of the *Morchella esculenta* fruit bodies that have been treated through the colloid mill is transferred to a stainless steel enzymolysis tank, heated to 50-60° C., adjusted to pH 4.5-6.0, and 0.05 to 0.1% cellulase, 0.01 to 0.1% beta-glucanase, and 0.01 to 0.1% protease by weight of the *Morchella esculenta* fruit bodies are added therein, to carry out the enzymolysis for 0.5 to 1.5 h with heat preservation and continuous stirring; and (4) drying, wherein fermented liquor after the enzymolysis is filtered and then dried to obtain the *Morchella esculenta* zymolytic powders.

The drying may be in the form of conventional spray drying, freeze drying and the like.

The cryoprotectant is composed of skim milk powder, trehalose, and maltodextrin.

Capsule products of the present invention comprise *Lactobacillus plantarum*, preferably the strain tlj-2014, which is preserved on Jul. 2, 2014, in China General Microbiological Culture Collection Center of Microbe Preservation Management Committee (CGMCC for short, address: No. 3, No. 1 Yard, West Beichen Road, Chaoyang District, Beijing City, China, 100101), with a classification designation of *Lactobacillus plantarum*, and a preservation number of CGMCC NO. 9405.

The *Lactobacillus plantarum* CGMCC No. 9405 strain in the present invention has physiologic features as follows. When examined under a microscope, the strain is short-rod-shaped, positive in Gram stain, atrichia, and produces no spore; and on solid media, its bacterial colony is white, smooth on the surface, dense, circular in morphology, and neat on the edge.

The strain is physicochemically characterized in that: catalase (−), gelatin liquefaction (−), indole experiment (+), motility (−), fermentation gas-production (−), nitrite reduction (−), fermentation gas-production (−), production of hydrogen sulfide gas (−), growth in a pH 4.0 MRS culture medium (+). ((−) denotes negative in the reaction result, and (+) denotes positive in the reaction result.)

The above *Lactobacillus plantarum* capsule product is obtained by the following method:

1) preparation of the core material, wherein 3 to 5% stachyose and 5 to 8% *Morchella esculenta* zymolytic powder by mass of the fermentation liquor are added into the *Lactobacillus plantarum* fermentation liquor that has been subjected to fermental cultivation in the fermentation tank, then the solution is mixed with a cryoprotectant solution, prefrozen at −50° C. for 0.5 h, followed by lyophilization in a vacuum freeze drier for 10 to 18 h, and then ground and pulverized to produce the core material;

a ratio of the fermentation liquor to the cryoprotectant solution is 1:1.4 to 0.8; the cryoprotectant solution is composed of skim milk powder, trehalose, and maltodextrin solutions; and the three solutions have a ratio by volume of skim milk powder:trehalose:maltodextrin=3:1:0.5;

the skim milk powder, trehalose, and maltodextrin solutions have concentrations of 5% skim milk powder, 1% trehalose, and 2% maltodextrin, respectively.

2) Coating, wherein the core material is suspended in a fluidized bed, and the wall material is coated thereon by spray in a manner that, a mixed solution of chitosan, glycerin and trehalose is sprayed from one sprayer, and a mixed solution of xanthan gum, carrageenin and zymolytic soybean protein isolate is sprayed from another sprayer, controlled at the same spray rate, and in the coating process, the temperature within the fluidized bed is between 25 and 38° C., and the capsule is formed after 30 min. The present invention further provides use of the *Lactobacillus plantarum* capsule product as a feed additive. The capsule product as a feed additive according to the present invention may have wide applications in various animal feed, but preferably in feed for poultry animals. The capsule product of the present invention is added into the feed in an amount of 3 to 5%, or used at 10 to 20 g for each livestock or poultry per day.

Beneficial Effects:

Modified soybean protein isolate is added into the wall material of the *lactobacillus* microcapsule provided herein. The modified soybean protein isolate has emulsifying capacity increased by 25%, and gelling capacity increased by 15-25% as compared with soybean protein isolate. The coordinated use of the modified soybean protein isolate, xanthan gum and carrageenin as well as chitosan increases gel strength by more than 10%, and enhances resistance of the capsule to gastric acid. Due to the employment of the modified soybean protein isolate, the capsule of the present invention has very good enteric solubility, and can be completely disintegrated to release *Lactobacillus plantarum* within 1 to 1.5 h after the capsule reaches the intestinal tract, then the *Lactobacillus plantarum* proliferates rapidly to become a dominant bacterial colony, thereby achieving the effects of inhibiting growth of pathogenic germs, and the like.

The present invention is compounded by utilizing *Morchella esculenta* zymolytic powders, and after zymolytic treatment, it not only allows nutritional ingredients thereof to effectively release into the product, but also allows the specific fragrance of *Morchella esculenta* to effectively release through enzymolysis, to allow the product to have trophic nature of *Morchella esculenta* as well.

DETAILED DESCRIPTION OF THE PREFERRED EMBODIMENTS

Example 1

A breeding process of *Lactobacillus plantarum* CGMCC No. 9405 employed in the present invention was as follows.

Original starting strains→activation in test tubes→diethyl sulfate (DES) mutagenesis→nitrosoguanidine (NTG) mutagenesis→plasma mutagenesis→primary screening on flat plates→secondary screening in shake flasks→passage stability test.

The starting strains employed in the present invention produced lactic acid at a rate of 1.5 g/L in an MRS glucose culture medium, and when the culture medium has a pH value of 3.5, the strains stopped growing, and had a decomposition rate of 0.34 mg/h/kg cabbage for sodium nitrite. The starting strains were collected by LI Zheng from ensilage at a fattening sheep farm in Yanchi County, Ningxia, on Sep. 15, 2013.

In order to increase its lactic acid production rate, acid resistance and nitrite decomposition rate, DES and NTG techniques were employed successively to perform mutagenesis on the strains. After the mutagenesis, the strains were subjected to primary screening employing MRS calcium carbonate plates, and then fermented employing 500-mL shake flasks. High-yielding strains were subjected to secondary screening by a biosensor analyzer, to select breed excellent strains of *Lactobacillus plantarum*, and then passage experiments were performed to evaluate hereditary stability thereof.

Hereditary stability results of *Lactobacillus plantarum* tlj-2014 showed that, through ten serial passages, each performance index was relatively stable, heredity was good, without reversion of behaviors, and thus *Lactobacillus plantarum* tlj-2014 was considered as a target strain obtained by select breeding.

It was found by validation that, the mutagenic strain might produce lactic acid at a rate up to 35 g/L/d, and the strain produced lactic acid at a concentration up to 95 g/L after fermentation for 71 h; and the strain was capable of surviving at a condition of pH 1.80. The strain degraded nitrite at a high rate, with decomposition capacity up to 9.8 mg/h/kg (nitrite is accumulated at a rate of about 1.1 mg/h/kg in a natural fermantation process), and could withstand 1% bile salt.

1) DES Mutagenesis and Select Breeding a. One ring of *Lactobacillus plantarum* L (a starting bacterium) on a test tube slant on a super-clean bench was taken, inoculated into a 250-mL triangular flask charged with 50 mL of the culture medium MRS (without agar, with 20 g/L glucose), and cultured at 200 rpm and 37° C. for about 12 h, to allow the bacterial bodies to be in an early-log growth phase.

b. 5 mL of the bacterium liquid was taken, centrifugated for 10 min at 5000 rpm to collect bacterial bodies, and the bacterial bodies were washed with normal saline twice.

c. The bacterial bodies were diluted with a pH 7.0 phosphate buffer to $10^7$/mL bacterium suspension.

d. 32 mL of a pH 7.0 potassium phosphate buffer, 8 mL of the bacterium suspension, and 0.4 mL of DES were taken, and intensively mixed in a 150-mL triangular flask into which a rotor was placed in advance, to allow DES to have a final concentration of 1% (v/v).

e. The mixture was reacted in a shaker at 37° C. and 150 rpm for 30 min, and 1 mL of the mixed solution was taken, into which was added 0.5 mL of a 25% $Na_2S_2O_3$ solution to stop the reaction.

f. Appropriate dilution was carried out, 0.2 mL of bacterium liquid at the final dilution was taken, and coated into a calcium carbonate screening culture medium (a calcium carbonate MRS culture medium containing 100 g/L glucose) plate. After cultured at 37° C. for 2 to 3 days, the strains on the screening plate were transferred, employing photolithography, onto LPHMRS culture media (modified MRS culture media at low pH values) at pH 1.5, 1.8 and 2.0, and onto a sodium nitrite screening culture medium (the single nitrogen source was a modified MRS screening culture medium containing 2 g/L sodium nitrite).

g. After cultured at 37° C. for 2 to 3 days, larger bacterial colonies were picked out that can grow on the LPHMRS culture medium, sodium nitrite screening culture medium and the calcium carbonate screening culture medium, respectively. Via preliminary screening, a bacterial colony picked out was designated as *Lactobacillus plantarum* L1.

2) Nitrosoguanidine Mutagenesis a. One ring of *Lactobacillus plantarum* L1 on a test tube slant on a super-clean bench was taken, inoculated into a 250-mL triangular flask charged with 50 mL of the culture medium MRS (without agar, with a glucose concentration of 60 g/L), and cultured at 200 rpm and 37° C. for about 12 h, to allow the bacterial bodies to be in an early-log growth phase.

b. 5 mL of the bacterium liquid was taken, centrifugated for 10 min at 5000 rpm to collect bacterial bodies, and the bacterial bodies were washed with normal saline twice.

c. The bacterial bodies were diluted with a pH 6.0 phosphate buffer to $10^7$/mL bacterium suspension.

d. 10 mL of the bacterium suspension was taken and transferred into a 100-mL triangular flask, and 10 mg of NTG was added therein, to formulate an NTG solution at a final concentration of 10 mg/mL, and 4 to 5 drops of acetone were added therein to favor the dissolution of NTG.

e. The reaction was shaken for 30 min at 37° C. and 200 rpm, centrifugated for 10 min at 5000 rpm to collect bacterial bodies, and the bacterial bodies were washed several times with sterile normal saline to stop the reaction.

f. Appropriate dilution was carried out, 0.2 mL of bacterium liquid at the final dilution was taken, and coated into a calcium carbonate screening culture medium (a calcium carbonate MRS culture medium containing 100 g/L glucose) plate. After cultured at 37° C. for 2 to 3 days, the strains on the screening plate were transferred, employing photolithography, onto LPHMRS culture media (modified MRS culture media at low pH values) at pH 1.5, 1.8 and 2.0, and onto a sodium nitrite screening culture medium (the single nitrogen source was a modified MRS screening culture medium containing 2 g/L sodium nitrite).

g. Strains were picked out by a method including: picking out larger bacterial colonies that can grow on the LPHMRS culture medium, sodium nitrite screening culture medium and the calcium carbonate screening culture medium, respectively. Via preliminary screening, 100 bacterial colonies in compliance with the above requirements were picked out.

3) Secondary Screening in Shake Flasks a. One ring of *Lactobacillus plantarum* on each test tube slant on a super-clean bench was taken respectively, inoculated into a 250-mL triangular flask charged with 50 mL of the culture medium MRS (without agar, with a glucose concentration of 100 g/L), and cultured at 200 rpm and 37° C. for about 15 h, to allow the bacterial bodies to be in a mid-log growth phase.

b. 5 mL of bacterium liquid was taken respectively, inoculated into a plate charged with 50 mL of a calcium carbonate screening liquid culture medium (a calcium carbonate MRS culture medium containing 250 g/L glucose), LPHMRS culture media (modified MRS culture media at low pH values) at pH 1.5, 1.8 and 2.0, and a sodium nitrite liquid screening culture medium (the single nitrogen source was a modified MRS screening culture medium containing 2 g/L sodium nitrite) (note: employing a 250-mL triangular flask). The mixture was cultured at 200 rpm and 37° C. for 3 to 4 days, the calcium carbonate screening liquid culture medium was detected for the L-lactic acid production rate, the LPHMRS liquid culture medium was detected for biomass, and the sodium nitrite liquid screening culture medium was detected for the nitrite consumption rate every day, respectively. After completion of the fermentation, the L-lactic acid production rates in the calcium carbonate screening liquid culture medium, biomass in the LPHMRS liquid culture medium, and the nitrite consumption rates in the sodium nitrite liquid screening culture medium were compared among 100 strains.

c. Strains having high L-lactic acid production rates, resistance to low pH (the strain could only grow in culture media at the lowest pH value of 1.8) and high nitrite consumption rates were selected, and designated as L2 strains.

4) Hereditary Stability Test

The L2 strains were passaged 10 times continuously on a slant, and detected for the fermentation situation after each passage, using a method of secondary screening in shake flasks. Experiments showed that, after 10 continuous passages on the slant, the strain had no evident changes in behaviors thereof, and each performance index was normal, indicating that the strain had strong hereditary stability. The strain was designated as *Lactobacillus plantarum* tlj-2014.

5) 5-L Fermentation Tank Test a. One ring of *Lactobacillus plantarum* L2 on each slant was taken, inoculated into a 250-mL triangular flask charged with 50 mL of the culture medium MRS (without agar, with a glucose concentration of 150 g/L), and cultured at 200 rpm and 37° C. for about 12 h, to allow the bacterial bodies to be in a mid-log growth phase.

b. Strains at the log phase were inoculated into a 5-L fermentation tank charged with 3 L of the MRS liquid culture medium (with initial glucose at 150 g/L). The inoculum concentration was 10%, the culture was performed at 37° C. and 100 rpm for 8 h, dissolved oxygen at the early-log phase was controlled at 10% (with aeration at 0.5 L/min), and anaerobic culture was performed for 63 h at the later phase. After completion of the fermentation, *Lactobacillus plantarum* L2 produced lactic acid up to 95 g/L.

c. Strains at the log phase were inoculated into a 5-L fermentation tank charged with 3 L of a pH 1.8 LPHMRS liquid culture medium (with initial glucose at 50 g/L). The inoculum concentration was 10%, the culture was performed at 37° C. and 100 rpm for 8 h, dissolved oxygen at the early-log phase was controlled at 10% (with aeration at 0.5 L/min), and anaerobic culture was performed at the later phase. During the whole process, the fermentation liquor was controlled at pH 1.8 with 0.5 mol/L sodium hydroxide, and the total culture time was 48 h. After completion of the fermentation, biomass of *Lactobacillus plantarum* L2 was detected to be 2.5 g/L, indicating that *Lactobacillus plantarum* L2 could survive in an environment at pH 1.8.

d. Strains at the log phase were inoculated into a 5-L fermentation tank charged with 3 L of a sodium nitrite liquid screening culture medium (the single nitrogen source was a modified MRS screening culture medium containing 2 g/L sodium nitrite). The inoculum concentration was 10%, the culture was performed at 37° C. and 100 rpm for 8 h, dissolved oxygen at the early-log phase was controlled at 10% (with aeration at 0.5 L/min), and anaerobic culture was performed at the later phase. In the fermentation process, according to the nitrite consumption rate, a 20 g/L sodium nitrite solution was sequentially added therein, and the mixture was cultured for 2 to 3 days. After completion of the fermentation, the degradation rate of sodium nitrite by *Lactobacillus plantarum* L2 in the fermentation process was calculated. Results showed that, under this condition, the degradation rate of sodium nitrite by L2 might be up to 563 mg/h/L.

Example 2

The *Lactobacillus plantarum* capsule product consisted of a wall material, *Lactobacillus plantarum*, a cryoprotectant, stachyose, and *Morchella esculenta* zymolytic powders.

The wall material was composed of zymolytic soybean protein isolate, chitosan, xanthan gum, carrageenin, glycerin and trehalose; and when formulated into a mixed solution, the above substances had concentrations of 10% zymolytic soybean protein isolate, 1% chitosan, 3% xanthan gum, 0.1% carrageenin, 0.5% glycerin, and 0.5% trehalose, respectively.

The zymolytic soybean protein isolate was prepared by a method including: formulating a solution of soybean protein isolate at a concentration of 10 to 13%, heating to 30-33° C., adjusting the solution to pH 3-5, added therein an acid proteinase at 0.2% by weight of the soybean protein isolate for enzymolysis with heat preservation for 1.5 h, and then spray drying the solution to obtain the zymolytic soybean protein isolate.

The *Lactobacillus plantarum* was a strain with a preservation number of CGMCC NO. 9405.

The *Morchella esculenta* zymolytic powders were prepared by a method as follows:

(1) drying and pulverizing fruit bodies of *Morchella esculenta*;

(2) homogeneous dissolution in water, wherein the pulverized fruit bodies of *Morchella esculenta* were added into a stainless steel cylinder, water 3 times by weight of the fruit bodies was added therein, to soak the fruit bodies for 5 h, and then this solution of the *Morchella esculenta* fruit bodies was passed through a colloid mill, under an operation condition of: a gap between a stator and a rotor of the colloid mill adjusted to 0.6±1 μm, and a flow rate of the colloid mill at 0.5 t/h;

(3) enzymolysis at rised temperature, wherein the mixed solution of the *Morchella esculenta* fruit bodies that had been treated through the colloid mill was transferred to a stainless steel enzymolysis tank, heated to 50° C., adjusted to pH 6.0, and 0.05% cellulase, 0.01% beta-glucanase, and 0.1% protease by weight of the *Morchella esculenta* fruit bodies were added therein, to carry out the enzymolysis for 1.5 h with heat preservation and continuous stirring; and (4) drying, wherein fermented liquor after the enzymolysis was filtered and then spray dried to obtain *Morchella esculenta* zymolytic powders.

The above *Lactobacillus plantarum* capsule product was prepared by a process as follows:

1) preparation of the core material, wherein 3% stachyose and 8% *Morchella esculenta* zymolytic powder by mass of the fermentation liquor were added into the *Lactobacillus plantarum* fermentation liquor that had been subjected to fermental cultivation in the fermentation tank, then the solution was mixed with a cryoprotectant solution, prefrozen at −50° C. for 0.5 h, followed by lyophilization in a vacuum freeze drier for 10 h, and then ground and pulverized to produce the core material; a ratio of the fermentation liquor to the cryoprotectant solution was 1:1.4; the cryoprotectant solution was composed of skim milk powder, trehalose, and maltodextrin solutions; and the three solution had a ratio by volume of skim milk powder:trehalose:maltodextrin=3:1: 0.5; and the skim milk powder, trehalose, and maltodextrin solutions had concentrations of 5% skim milk powder, 1% trehalose, and 2% maltodextrin, respectively.

2) Coating, wherein the core material was suspended in a fluidized bed, and the wall material was coated thereon by spray in a manner that, a mixed solution of chitosan, glycerin and trehalose was sprayed from one sprayer, and a mixed solution of xanthan gum, carrageenin and zymolytic soybean protein isolate was sprayed from another sprayer, controlled at the same spray rate, and in the coating process, the temperature within the fluidized bed was 28° C., and the capsule was formed after 30 min.

Example 3

The *Lactobacillus plantarum* capsule product consisted of a wall material, *Lactobacillus plantarum*, a cryoprotectant, stachyose, and *Morchella esculenta* zymolytic powders.

The wall material was composed of zymolytic soybean protein isolate, chitosan, xanthan gum, carrageenin, glycerin and trehalose; and when formulated into a mixed solution, the above substances had concentrations of 7% zymolytic soybean protein isolate, 2% chitosan, 1% xanthan gum, 0.5% carrageenin, 1% glycerin, and 2% trehalose, respectively.

The zymolytic soybean protein isolate was prepared by a method including: formulating a solution of soybean protein isolate at a concentration of 10 to 13%, heating to 42-45° C., adjusting the solution to pH 5, added therein an acid proteinase at 1% by weight of the soybean protein isolate for enzymolysis with heat preservation for 0.5 h, and then spray drying the solution to obtain the zymolytic soybean protein isolate.

The *Morchella esculenta* zymolytic powders were prepared by a method as follows:

(1) drying and pulverizing fruit bodies of *Morchella esculenta;*

(2) homogeneous dissolution in water, wherein the pulverized fruit bodies of *Morchella esculenta* were added into a stainless steel cylinder, water 6 times by weight of the fruit bodies was added therein, to soak the fruit bodies for 3 h, and then this solution of the *Morchella esculenta* fruit bodies was passed through a colloid mill, under an operation condition of: a gap between a stator and a rotor of the colloid mill adjusted to 1 μm, and a flow rate of the colloid mill at 1 t/h;

(3) enzymolysis at rised temperature, wherein the mixed solution of the *Morchella esculenta* fruit bodies that had been treated through the colloid mill was transferred to a stainless steel enzymolysis tank, heated to 60° C., adjusted to pH 4.5, and 0.1% cellulase, 0.1% beta-glucanase, and 0.01% protease by weight of the *Morchella esculenta* fruit bodies were added therein, to carry out the enzymolysis for 0.5 h with heat preservation and continuous stirring; and (4) drying, wherein fermented liquor after the enzymolysis was filtered and then freeze dried in vacuum to obtain the *Morchella esculenta* zymolytic powders.

The above *Lactobacillus plantarum* capsule product was prepared by a process as follows:

1) preparation of the core material, wherein 3% stachyose and 8% *Morchella esculenta* zymolytic powder by mass of the fermentation liquor were added into the *Lactobacillus plantarum* fermentation liquor that had been subjected to fermental cultivation in the fermentation tank, then the solution was mixed with a cryoprotectant solution, prefrozen at −50° C. for 0.5 h, followed by lyophilization in a vacuum freeze drier for 10 to 18 h, and then ground and pulverized to produce the core material;

a ratio of the fermentation liquor to the cryoprotectant solution was 1:0.8; the cryoprotectant solution was composed of skim milk powder, trehalose, and maltodextrin solutions; and the three solution had a ratio by volume of skim milk powder:trehalose:maltodextrin=3:1:0.5; and 2) coating, wherein the core material was suspended in a fluidized bed, and the wall material was coated thereon by spray in a manner that, a mixed solution of chitosan, glycerin and trehalose was sprayed from one sprayer, and a mixed solution of xanthan gum, carrageenin and zymolytic soybean protein isolate was sprayed from another sprayer, controlled at the same spray rate, and in the coating process, the temperature within the fluidized bed was 38° C., and the capsule was formed after 30 min.

*Lactobacillus plantarum* was a strain with a preservation number of CGMCC NO. 9405.

Example 4

Test for resistance of the *Lactobacillus plantarum* capsule product to bile salts.

Capsule products from Examples 2 to 3 were placed into a pig bile salt solution at 37° C. (at a solution concentration of 3.0%), kept at this temperature, and stirred continuously. After 2 h, the capsule products were taken out, washed with sterile normal saline, dissolved with a capsule dissolving solution, determined for the survival rate of lactobacilli, and compared with unembedded bacterium liquid. Test results are as shown in the following table.

| | Morphological change | Survival rate |
|---|---|---|
| Example 1 | Not disintegrated | 87.5% |
| Example 2 | Not disintegrated | 89.3% |
| Uncoated control | — | 0.65% |

Example 5

Test of use effect of the product from Example 2 in the present invention applied in feed additives for nursing sows.

A pig farm was selected in Ningxia to carry out feeding tests for duration of 21 days. The tests employed a single-factor comparison design, wherein 50 healthy nursing sows with similar farrowing numbers and average birth weight, and all with 2 or 3 fetal times, were randomly selected, and randomly divided into 2 groups (i.e., a test group and a control group), with 15 replicates in each group. Wherein, the test group had the present product capsules prepared in Example 2 added into the daily ration, and the control group had the like products on the market added therein. Weaning weight, diarrhea rates, and mortality rates of the piglets were recorded. Experimental results are as shown in the following table.

| Items | Test group | Control group |
|---|---|---|
| Number born alive | 10.9 | 11.0 |
| Average birth weight (kg) | 1.46 | 1.48 |
| 21-day weaning piglets | 10 | 8.30 |
| 21-day weaning weight of litter (kg) | 66.4 | 44.4 |
| 21-day weaning average weight (kg) | 6.64 | 5.35 |
| Net weight gain per piglet (kg) | 5.18 | 3.87 |
| Piglet diarrhea rate (%) | 6.1 | 11.3 |
| Mortality rate (%) | 1.7 | 4.1 |

Experimental results showed that, products of the present invention could ameliorate immunocompetence of sow and piglet organisms, reduce antibiotic consumption, and increase the breeding quality and benefit.

Example 6

Test of effect of the product from Example 2 in the present invention applied in feed additives for feeding weaning chicks.

The test was carried out at a certain chicken farm in Ningxia, and employed a single-factor experimental design, wherein 600 1-day-aged chicks each with body weight of (35±1) g were selected, and randomly divided into a control group of 300 chicks and a test group of the present invention of 300 chicks, with 3 replicates provided in each group, and 100 chicks in each replicate. A certain top-quality broodtime feed for chicks on the market was selected and fed to the control group, and the product from Example 2 of the present invention added on the basis of this feed was fed to the test group. During the test period, other environmental conditions were all kept identical and in compliance with the feeding and management standards for chicks.

The test period was 4 weeks, and determined indexes included: body weight, feed intake, survival rate, and incidence rate. Experimental results are as shown in the following table.

| Items | Control group | Test group of the present invention |
|---|---|---|
| Number of tested chicks | 300 | 300 |
| Birth weight of chicks (g) | 35 ± 1 | 35 ± 1 |
| Body weight at the 4$^{th}$ weekend (g) | 415.56 ± 2.25 | 640.50 ± 3.42 |
| Feed intake (g) | 517.30 ± 0.67 | 568.27 ± 0.73 |
| Survival rate (%) | 96.33 | 99.00 |
| Incidence rate (%) | 5.33 | 2.33 |

Experimental results showed that, after fed for 4 weeks, chicks in the test group of the present invention had body weight and feed intake both apparently higher than those of the control group, indicating that the product of the present invention could promote digestion and enhance appetite, which contributed to growth and development of the poultry. Chicks in the test group of the present invention also had significant advantages over those in the control group in terms of survival rate and incidence rate of the chicks, indicating that the product of the present invention could help ameliorate the digestive system environment of livestock and poultry, effectively inhibit the growth of pathogenic germs, improve immunity, and reduce the fatality rate.

The invention claimed is:

1. A *Lactobacillus plantarum* capsule, comprising:
a core material; and
a coating material covering the core material,
wherein the core material comprises:
*Lactobacillus plantarum* having a Deposit No. CGMCC NO.9405 at China General Microbiological Culture Collection Center;
a cryoprotectant comprising skim milk powder, trehalose and maltodextrin;
stachyose; and
Morchella *esculenta* zymolytic powders,
wherein the coating material comprises:
zymolytic soybean protein isolate;
chitosan;
xanthan gum;
carrageenan;
glycerin; and
trehalose,
and wherein the coating material is applied as a solution comprising by weight 7 to 10% zymolytic soybean protein isolate, 1 to 2% chitosan, 1 to 3% xanthan gum, 0.1 to 0.5% carrageenin, 0.3 to 1% glycerin, and 0.5 to 2% trehalose.

2. The *Lactobacillus plantarum* capsule of claim 1, wherein the zymolytic soybean protein isolate is prepared by a method comprising the steps of:
formulating a solution of soybean protein isolate at a concentration of 10 to 13%; heating the solution to 30-45° C.;
adjusting the solution to pH 3-5;
adding an acidic proteinase at 0.1 to 1% by weight of the soybean protein isolate to form an enzymolysis solution;
incubating the enzymolysis solution for 0.5 to 1.5 h, and then
spray drying the enzymolysis solution to obtain the zymolytic soybean protein isolate.

3. The *Lactobacillus plantarum* capsule of claim 2, wherein the *Lactobacillus plantarum* capsule is prepared by a method
comprising the steps of:
preparing the core material by adding stachyose and *Morchella esculenta* zymolytic powder to a *Lactobacillus plantarum* fermentation liquor to form a first mixture, wherein stachyose is added in an amount of 3 to 5% by weight of the fermentation liquor and *Morchella esculenta* zymolytic powder is added in an amount of 5-8% by weight of the fermentation liquor, adding a cryoprotectant solution to the first mixture to form a second mixture, freezing the second mixture at −50° C. for 0.5 h, lyophilizing frozen second mixture in a vacuum freeze drier for 10 to 18 h, grounding and pulverizing the lyophilized second mixture to produce the core material, wherein the cryoprotectant solution is prepared by mixing a skim milk powder solution, a trehalose solution, and a maltodextrin solution at a volume ratio of 3:1:0.5;
suspending the core material in a fluidized bed; and
spray coating the suspended core material with a first solution comprising chitosan, glycerin and trehalose and a second solution comprising xanthan gum, carrageenin and zymolytic soybean protein isolate, wherein the first solution is sprayed from a first sprayer at a first spray rate and the second solution is sprayed from a second sprayer at the same spray rate as the first spray rate, wherein the fluidized bed is maintained at a temperature between 25° C. and 38° C., and wherein the capsule is formed after 30 min.

4. The *Lactobacillus plantarum* capsule of claim 1, wherein the *Morchella esculenta* zymolytic powders are prepared by a method comprising the steps of:
drying and pulverizing fruit bodies of *Morchella esculenta*;
placing pulverized fruit bodies of *Morchella esculenta* into a stainless steel cylinder;
adding water to the stainless steel cylinder in an amount of 3 to 6 times by weight of the fruit bodies of *Morchella esculenta*;
soaking the pulverized fruit bodies for 3 to 5 h, and then passing the soaked fruit bodies of *Morchella esculenta* through a colloid mill with a gap of 0.5-1 μm between a stator and a rotor of the colloid mill, and a flow rate of 0.4-1 ton/hour to produce a colloid;

transferring the colloid to a stainless steel enzymolysis tank;

heating the colloid to 50-60° C.;

adjusting the colloid to pH 4.5-6.0;

adding 0.05 to 0.1% cellulase, 0.01 to 0.1% beta-glucanase and 0.01 to 0.1% protease by weight of the fruit bodies of Morchella esculenta to form an enzymolysis mixture;

incubating the enzymolysis mixture for 0.5 to 1.5 h under continuous stirring; and filtering the incubated enzymolysis mixture and drying the filtered enzymolysis mixture to obtain the Morchella esculenta zymolytic powders.

5. The Lactobacillus plantarum capsule of claim 4, characterized in that the Lactobacillus plantarum capsule is prepared by a method comprising the steps of:

preparing the core material by adding stachyose and Morchella esculenta zymolytic powder to a Lactobacillus plantarum fermentation liquor to form a first mixture, wherein stachyose is added in an amount of 3 to 5% by weight of the fermentation liquor and Morchella esculenta zymolytic powder is added in an amount of 5-8% by weight of the fermentation liquor, adding a cryoprotectant solution to the first mixture to form a second mixture, freezing the second mixture at −50° C. for 0.5 h, lyophilizing frozen second mixture in a vacuum freeze drier for 10 to 18 h, grounding and pulverizing the lyophilized second mixture to produce the core material, wherein the cryoprotectant solution is prepared by mixing a skim milk powder solution, a trehalose solution, and a maltodextrin solution at a volume ratio of 3:1:0.5;

suspending the core material in a fluidized bed; and spray coating the suspended core material with a first solution comprising chitosan, glycerin and trehalose and a second solution comprising xanthan gum, carrageenin and zymolytic soybean protein isolate, wherein the first solution is sprayed from a first sprayer at a first spray rate and the second solution is sprayed from a second sprayer at the same spray rate as the first spray rate, wherein the fluidized bed is maintained at a temperature between 25° C. and 38° C., and wherein the capsule is formed after 30 min.

6. The Lactobacillus plantarum capsule of claim 1, wherein the Lactobacillus plantarum capsule is prepared by a method comprising the steps of:

preparing the core material by adding stachyose and Morchella esculenta zymolytic powder to a Lactobacillus plantarum fermentation liquor to form a first mixture, wherein stachyose is added in an amount of 3 to 5% by weight of the fermentation liquor and Morchella esculenta zymolytic powder is added in an amount of 5-8% by weight of the fermentation liquor, adding a cryoprotectant solution to the first mixture to form a second mixture, freezing the second mixture at −50° C. for 0.5 h, lyophilizing the frozen second mixture in a vacuum freeze drier for 10 to 18 h, grounding and pulverizing the lyophilized second mixture to produce the core material, wherein the cryoprotectant solution is prepared by mixing a skim milk powder solution, a trehalose solution, and a maltodextrin solution at a volume ratio of 3:1:0.5; suspending the core material in a fluidized bed; and spray coating the suspended core material with a first solution comprising chitosan, glycerin and trehalose and a second solution comprising xanthan gum, carrageenin and zymolytic soybean protein isolate, wherein the first solution is sprayed from a first sprayer at a first spray rate and the second solution is sprayed from a second sprayer at the same spray rate as the first spray rate, wherein the fluidized bed is maintained at a temperature between 25° C. and 38° C., and wherein the capsule is formed after 30 min.

7. The Lactobacillus plantarum capsule of claim 6, wherein the fermentation liquor is mixed with the cryoprotectant solution at a ratio of 1:1.4-0.8.

8. The Lactobacillus plantarum capsule of claim 6, wherein the skim milk powder solution contains 5% skim milk powder, the trehalose solution contains 1% trehalose, and the maltodextrin solution contains 2% maltodextrin.

9. An animal feed additive, comprising the Lactobacillus plantarum capsule of claim 1.

* * * * *